(12) United States Patent
Kang (10) Patent No.: US 12,076,580 B2
(45) Date of Patent: Sep. 3, 2024

(54) APPARATUS FOR TREATING ATHLETE'S FOOT

(71) Applicant: SHENB Co., Ltd., Seoul (KR)

(72) Inventor: Sun-Young Kang, Seoul (KR)

(73) Assignee: SHENB Co., Ltd., Seoul (KR)

( * ) Notice: Subject to any disclaimer, the term of this patent is extended or adjusted under 35 U.S.C. 154(b) by 359 days.

(21) Appl. No.: 17/684,447

(22) Filed: Mar. 2, 2022

(65) Prior Publication Data
US 2022/0339463 A1 Oct. 27, 2022

(30) Foreign Application Priority Data

Apr. 26, 2021 (KR) .......................... 10-2021-0053673

(51) Int. Cl.
| | | |
|---|---|---|
| *A61N 5/067* | (2006.01) | |
| *A61F 7/00* | (2006.01) | |
| *A61L 2/10* | (2006.01) | |
| *A61L 2/26* | (2006.01) | |
| *A61N 5/06* | (2006.01) | |

(52) U.S. Cl.
CPC ................. *A61N 5/067* (2021.08); *A61F 7/00* (2013.01); *A61L 2/10* (2013.01); *A61L 2/26* (2013.01); *A61N 5/0624* (2013.01); *A61F 2007/0045* (2013.01); *A61L 2202/11* (2013.01); *A61L 2202/14* (2013.01); *A61N 2005/0626* (2013.01); *A61N 2005/0633* (2013.01); *A61N 2005/0642* (2013.01); *A61N 2005/0652* (2013.01); *A61N 2005/0663* (2013.01)

(58) Field of Classification Search
None
See application file for complete search history.

(56) References Cited

U.S. PATENT DOCUMENTS

| | | | |
|---|---|---|---|
| 6,776,790 B1 * | 8/2004 | Maruyama | A61N 5/0616 |
| | | | 607/94 |
| 2004/0158301 A1 * | 8/2004 | Tucek | A61N 5/0616 |
| | | | 607/89 |
| 2009/0143842 A1 * | 6/2009 | Cumbie | A61N 5/0624 |
| | | | 600/365 |

(Continued)

FOREIGN PATENT DOCUMENTS

| | | |
|---|---|---|
| KR | 10-2009-0037759 A | 4/2009 |
| KR | 10-1019520 B1 | 3/2011 |

(Continued)

*Primary Examiner* — Catherine M Voorhees
*Assistant Examiner* — James Moss
(74) *Attorney, Agent, or Firm* — Stein IP, LLC (57) ABSTRACT

An apparatus for treating athlete's foot. The apparatus includes: a main body having at least one body accommodating space part to accommodate a body portion of at least one of a hand and foot; a laser output unit mounted onto the main body, and provided to emit laser light from an upper side to a lower side of the body accommodating space part; and a laser swing unit driven so that the laser output unit swings on the main body, in which the laser output unit includes a first laser diode emitting laser light of a 405 nm wavelength and a second laser diode emitting laser light of a 635 nm wavelength. The apparatus is capable of treating athlete's foot generated on the hand, foot, nails, or toenails by using the light from a laser and/or an LED having a wavelength band useful for treating athlete's foot.

15 Claims, 9 Drawing Sheets

(56) References Cited

U.S. PATENT DOCUMENTS

| | | | | |
|---|---|---|---|---|
| 2011/0213446 A1* | 9/2011 | Tucek | ............... | A61N 5/0616 |
| | | | | 607/89 |
| 2011/0224759 A1* | 9/2011 | Shanks | ................ | A61N 5/10 |
| | | | | 607/89 |
| 2017/0165499 A1* | 6/2017 | Blanche | .............. | A61N 5/062 |

FOREIGN PATENT DOCUMENTS

| | | | | |
|---|---|---|---|---|
| KR | 10-2012-0026609 A | 3/2012 | | |
| KR | 10-2012-0080037 A | 7/2012 | | |
| KR | 10-2013-0059331 A | 6/2013 | | |
| KR | 102056921 B1 * | 1/2020 | ......... | A61N 1/36014 |
| KR | 10-2079764 B1 | 2/2020 | | |

* cited by examiner

APPARATUS FOR TREATING ATHLETE'S FOOT

CROSS-REFERENCE TO RELATED APPLICATIONS

This application claims priority to and the benefit of Korean Patent Application No. 10-2021-0053673 filed in the Korean Intellectual Property Office on Apr. 26, 2021, the entire contents of which are incorporated herein by reference.

TECHNICAL FIELD

The present invention relates to an apparatus for treating athlete's foot, and more particularly, to an apparatus for treating athlete's foot, which is used for very effectively treating athlete's foot generated on the hands, feet, nails, or toenails by using a light source having a wavelength band useful for treating athlete's foot, and has the increased convenience of using the apparatus.

BACKGROUND ART

In general, athlete's foot is a superficial fungal disease caused by dermatophytes infecting the stratum corneum of the foot skin, and superficial mycosis is a disease caused by a fungus infecting the stratum corneum that is the outermost layer of the skin, or the nails or toenails.

As a method of treating athlete's foot, a drug treatment method using drugs in the form of taking drugs or applying the drug to the skin is mainly used, and athlete's foot in the toenails has difficulties such as not being easily treated even with the treatment with drugs, and depending on the physical constitution, sometimes side effects occur, which worsens health.

In addition, toenail athlete's foot causes thickening and discoloration of the toenails, as well as deformity of the toenails when toenail athlete's foot progresses to chronic condition, and if toenail athlete's foot is not treated, inflammation and pain may occur in the skin under or around the toenails, and it is more problematic in terms of beauty treatment as well as physical symptoms.

Therefore, an athlete's foot treatment device has been developed and released as a method for treating athlete's foot while resolving the difficulties of drug treatment, and a method of emitting ultraviolet (UV) light is mainly applied.

However, the athlete's foot treatment device in the related art adopts a method of simply emitting a light source, such as a laser or ultraviolet (UV), to the toe side, and has a disadvantage in that the treatment effect is low.

In the meantime, as the prior art, Korean Patent Nos. 10-2079764 and 10-1019520 disclose the apparatus for treating athlete's foot including a foot accommodating part.

PRIOR ART LITERATURE

Patent Document (Patent Document 1) Korean Patent No. 10-2079764
(Patent Document 1) Korean Patent No. 10-1019520

SUMMARY OF THE INVENTION

An object of the present invention is to provide an apparatus for treating athlete's foot, which is used for very effectively treating athlete's foot generated on the hands, feet, nails, or toenails by using a light source having a wavelength band useful for treating athlete's foot.

Another object of the present invention is to provide an apparatus for treating athlete's foot, which includes a configuration in which a laser light source having a wavelength band useful for treating athlete's foot, and allows a user to selectively use the equipped laser light source by a fixing method or a swing method, and is capable of treating athlete's foot through local emission or extensive emission.

Another object of the present invention is to provide an apparatus for treating athlete's foot, which is mounted with an Ultraviolet (UV) Light Emitting Diode (LED) to perform sterilization and disinfection of the inside of the apparatus, thereby making the apparatus clean to use, such as preventing internal contamination, and improving use convenience of the apparatus.

An exemplary embodiment of the present invention provides an apparatus for treating athlete's foot, the apparatus including: a main body having at least one body accommodating space part to accommodate a body portion of at least one of a hand and foot; a main body having at least one body accommodating space part to accommodate a body portion of at least one of a hand and foot; a laser output unit mounted onto the main body, and provided to emit laser light from an upper side to a lower side of the body accommodating space part; and a laser swing unit driven so that the laser output unit swings on the main body, in which the laser output unit includes a first laser diode emitting laser light of a 405 nm wavelength and a second laser diode emitting laser light of a 635 nm wavelength.

The apparatus may further include an LED light source unit mounted onto the main body and configured to emit LED light from the lower side to the upper side of the body accommodating space part, in which the LED light source unit includes a first LED emitting LED light of a 405 nm wavelength and a second LED emitting LED light of a 635 nm wavelength, and the first LED and the second LED are provided in plural to be disposed at intervals and sequentially arranged alternately.

The laser swing unit may include: a driving motor positioned at the upper side of the body accommodating space part and fixedly installed on the main body; a main bevel gear coupled to a rotation shaft of the driving motor; a first driven bevel gear cross-coupled to one side of the main bevel gear; a first connection link of which one end is link-coupled to the first driven bevel gear; a first swing driving body link-coupled to the other end of the first connection link to perform a swing operation and mounted with the first laser diode; a second driven bevel gear cross-coupled to the other side of the main bevel gear; a second connection link of which one end is link-coupled to the second driven bevel gear; and a second swing driving body link-coupled to the other end of the second connection link to perform a swing operation and mounted with the second laser diode.

The LED light source unit may be provided within a grooved mounting part recessed in a down direction on a bottom surface of the body accommodating space part, and the grooved mounting part may be covered by a tempered glass plate so as to allow LED light to transmit and emit, and the tempered glass plate may be disposed so as to maintain the same horizontal surface as the bottom surface of the body accommodating space part.

A display unit may be mounted on an upper surface of the main body, a camera unit photographing the body accommodating space part may be mounted, and the display unit may be installed to display photographing data of the camera unit to allow a user to monitor a treatment scene of the hand or foot in real time and allow the user to adjust a treatment position of the hand or foot.

An ultraviolet (UV) LED may be mounted onto the main body to self-sterilize an inside of the body accommodating space part.

An opening/closing door may be provided on the main body, and functions as an opening/closing member to open and close the body accommodating space part, and function as a support for stably supporting a rear part of the foot exposed to the outside when being stepped by accommodating the foot for treating athlete's foot of the foot or toenails in the body accommodating space part.

An inner surface of the opening/closing door and a bottom surface of the body accommodating space part may be made of a stainless steel or titanium material having harmless to human body, rigidity, and corrosion resistance.

The opening/closing door may be provided to perform an open/close operation on the main body through attachment/detachment by a magnet.

A planar heating body may be disposed in at least one of the opening/closing door and the body accommodating space part so as to provide heat.

A curtain part may be provided at an entrance part of the body accommodating space part.

The first LED emitting the LED light of the 405 nm wavelength and the second LED emitting the LED light of the 635 nm wavelength may alternately output the LED light according to a setting time.

The first LEDs emitting the LED light of the 405 nm wavelength may be disposed at intervals so that the emitted light overlaps, and the second LEDs emitting the LED light of the 635 nm wavelength are disposed at intervals so that the emitted light overlaps.

The body accommodating space part may be disposed at left and right sides in the main body and be divided by a partition wall to be provided with a first body accommodating space part and a second body accommodating space part, a first laser output unit and a first laser swing unit, and a second laser output unit and a second laser swing unit may be matched and provided to an upper side of the first body accommodating space part and an upper side of the second body accommodating space part, respectively, and the first laser output unit and the first laser swing unit, and the second laser output unit and the second laser swing unit are separately controlled or synchronously controlled.

An IR sensor may be mounted on the main body to detect entrance or location of the hand or foot when the hand or foot enters or is located in the body accommodating space part.

According to the present invention, it is possible to provide the apparatus for treating athlete's foot which is capable of very effectively treating athlete's foot generated on the hand, foot, nails, or toenails by emitting laser light by using a light source output of a laser and/or an LED having a wavelength band useful for treating athlete's foot, and has excellent use convenience.

According to the present invention, it is possible to provide the apparatus for treating athlete's foot which is equipped with the laser light source having a wavelength band useful for treating athlete's foot to selectively or essentially use the laser light source by a fixing method or a swing method through program control, and locally and intensively emits laser light or broadly and expansively emits laser light, thereby treating athlete's foot on a desired body portion.

According to the present invention, it is possible to provide the apparatus for treating athlete's foot which is capable of preventing internal contamination, such as the propagation of skin fungus according to the treatment of athlete's foot, and may be used cleanly by performing sterilization and disinfection inside the apparatus through the configuration of mounting the ultraviolet (UV) LED.

DETAILED DESCRIPTION

An exemplary embodiment of the present invention will be described with reference to the accompanying drawings, and an object and the configuration, and the features of the present invention will be understood well through the

DETAILED DESCRIPTION

An apparatus 1 for treating athlete's foot according to an exemplary embodiment of the present invention may include a main body 100, a laser output unit 200, and a laser swing unit 300 as illustrated in FIGS. 1 to 9.

In addition, the apparatus 1 for treating athlete's foot may further include an LED light source unit 400 and a display unit 500.

Further, a power supply unit 600 for use of the apparatus, and a control unit 700 for controlling a general operation of the apparatus and executing various commands input by a user are basically equipped, which are the obvious configuration.

The main body 100 is provided with at least one body accommodating space part 110 to accommodate the body portion of at least one of the hand and foot for treating athlete's foot inside the apparatus.

That is, the body accommodating space part 110 is formed so that a user easily pushes the body portion of the hand or foot from the front side of the main body 100 and the body portion of the hand or foot is accommodated inside the body accommodating space part 110, and one or two body accommodating space parts 110 may be formed.

Figure 1:
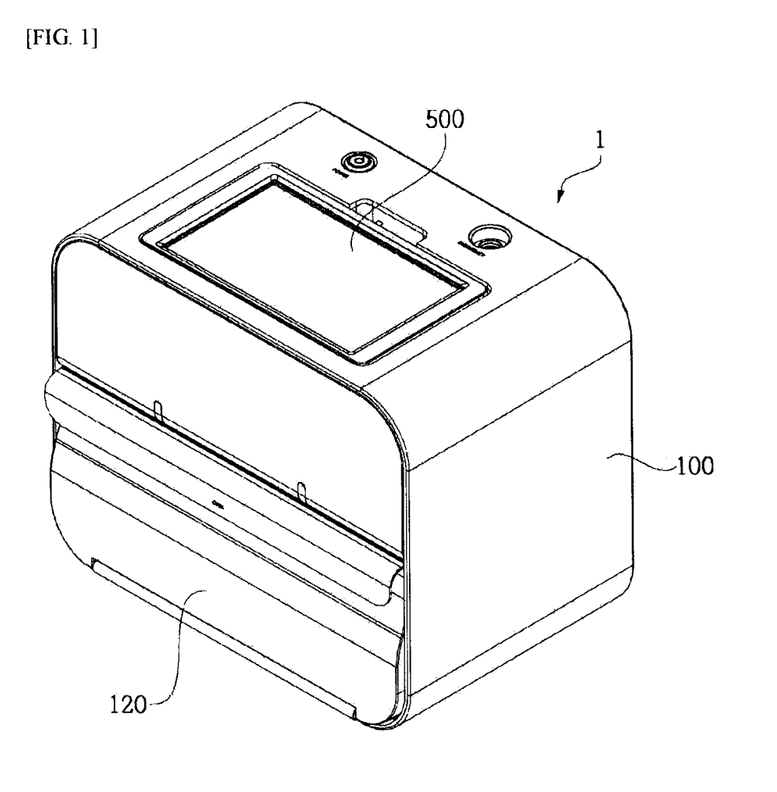
FIG. 1 is a diagram illustrating an example of an appearance of an apparatus for treating athlete's foot according to an exemplary embodiment of the present invention.
Figure 2:
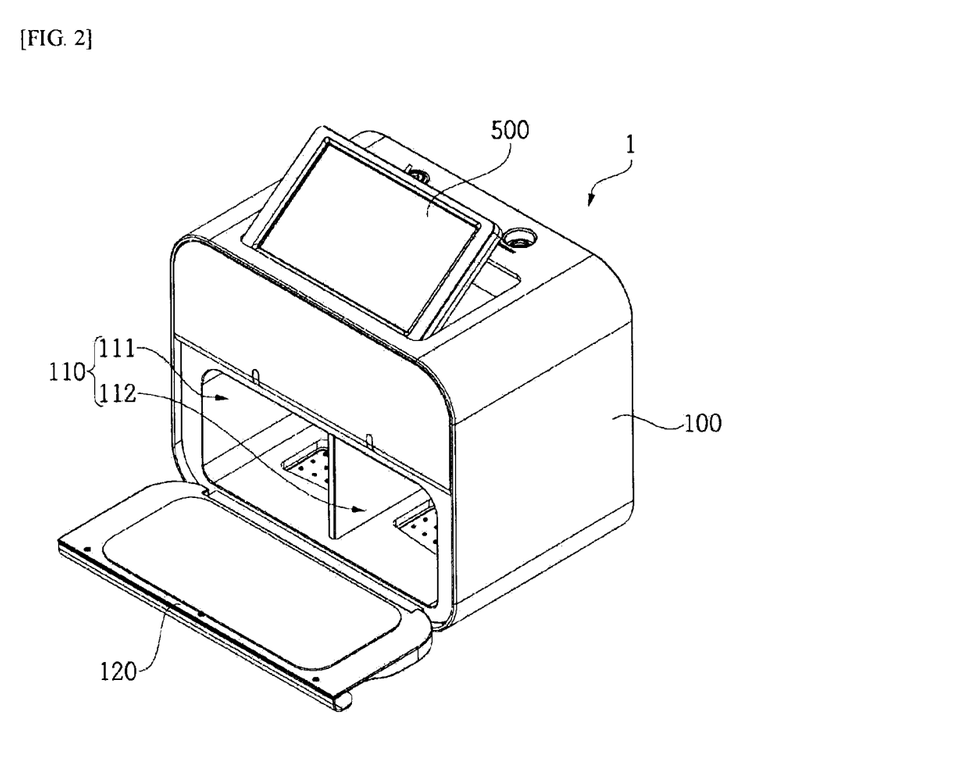
FIG. 2 is a perspective view illustrating an opening state of a body accommodating space part in the apparatus for treating athlete's foot according to the exemplary embodiment of the present invention.
Figure 3:
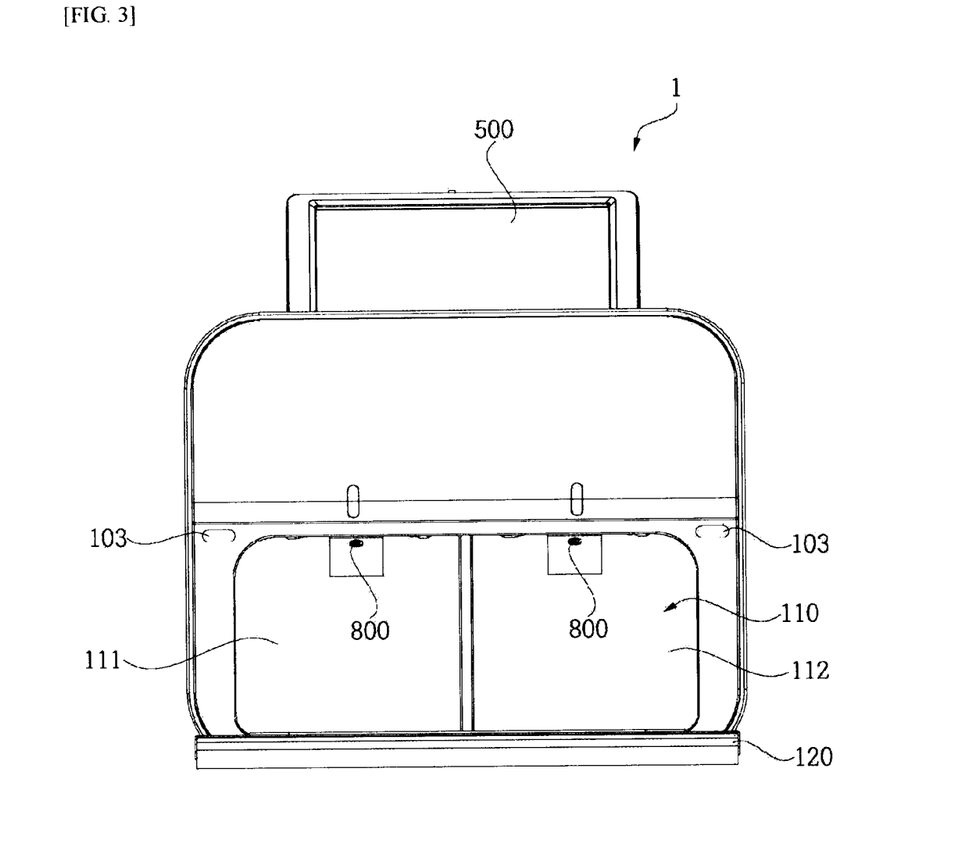
FIG. 3 is a front view illustrating the opening state of the body accommodating space part in the apparatus for treating athlete's foot according to the exemplary embodiment of the present invention.
Figure 4:
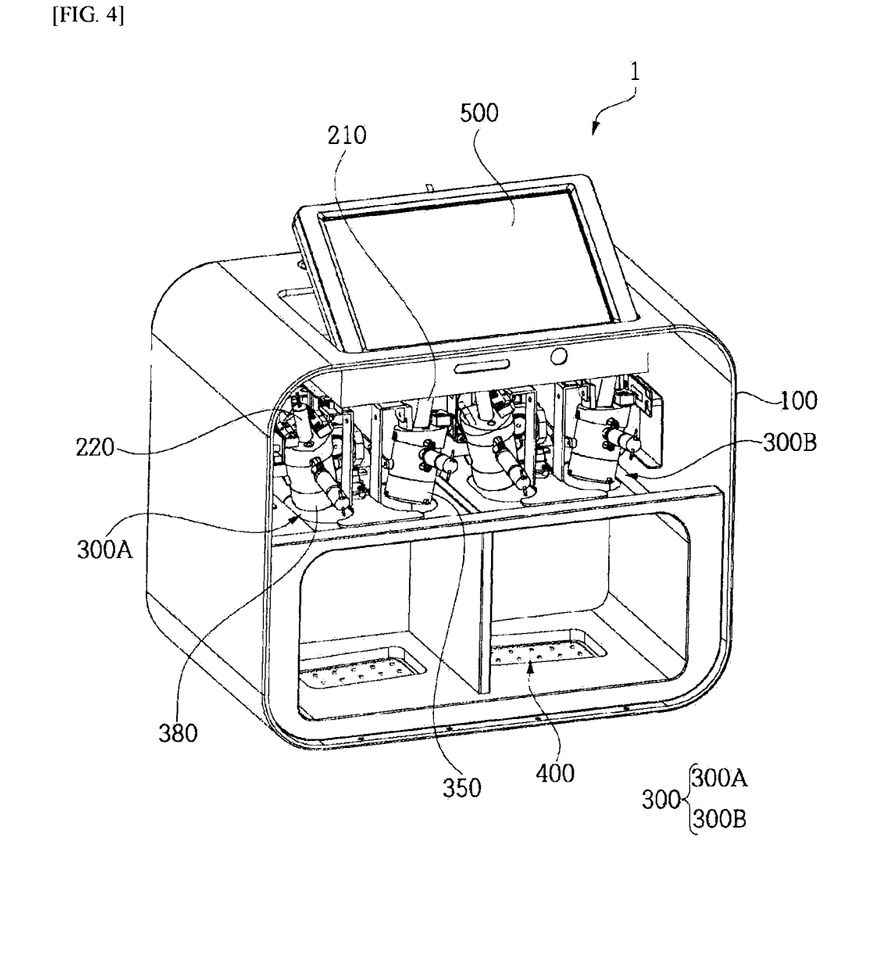
FIG. 4 is a configuration diagram illustrating a laser swing unit in the apparatus for treating athlete's foot according to the exemplary embodiment of the present invention.

For example, as illustrated in FIGS. 2 to 4, it is preferable that the body accommodating space part 110 is formed with two divided spaces, but the present invention is not particularly limited thereto.

In addition, the body accommodating space part 110 is disposed at left and right sides of the main body 100 and is divided by a partition wall to be provided with a first body accommodating space part 111 and a second body accommodating space part 112.

At an entrance part of the body accommodating space part 110, a curtain part (not illustrated) may be provided to prevent laser light from leaking to the outside and improve treatment efficiency during the treatment of athlete's foot.

The main body 100 may be provided in various shapes in consideration of the aspects of improvement of use convenience and design.

The laser output unit 200 is mounted on the main body 100, and is provided to emit laser light to treat athlete's foot from an upper side to a lower side of the body accommodating space part 110.

The laser output unit 200 includes a first laser diode 210 emitting laser light at a wavelength of 405 nm, and a second laser diode 220 emitting laser light at a wavelength of 635 nm.

The first laser diode 210 and the second laser diode 220 may be inclined relative to each other.

In this case, the 405 nm wavelength functions to kill bacteria, such as skin fungi, and the 635 nm wavelength serves to help expand blood vessels in the body portion and to expose the skin fungi to the outside.

In addition, a photochemical reaction of the laser output unit 200 emitting laser light of 405 nm and 635 nm wavelengths will be described below.

The 405 nm wavelength is the ultraviolet wavelength, which activates NADPH oxidase, that is the photoreceptor, and helps the generation of reactive oxygen species (ROS), and the generated reactive oxygen species (ROS) is converted into hydrogen peroxide ($H_2O_2$) in the body to destroy the fungal cell wall and thus kills the fungus.

The 635 nm wavelength activates cytochrome c oxidase (CCO) that is the photoreceptor to increase adenosine triphosphate (ATP) and reactive oxygen species (ROS), and the increase in adenosine triphosphate (ATP) activates the nitric oxide synthase (eNOS) pathway, and nitric oxide (NO) is generated, which not only destroys each cell of the fungus, but also improves blood circulation in the corresponding area. Further, reactive oxygen species (ROS) is rapidly converted into hydrogen peroxide ($H_2O_2$) to destroy the cell wall of the fungus and kill the fungus. That is, two types of immune cells serve to destroy the cell wall of the fungus by using hydrogen peroxide generated by photochemical reaction.

The laser swing unit 300 is the constituent element for driving the laser output unit 200 so as to swing on the main body 100.

Figure 5:
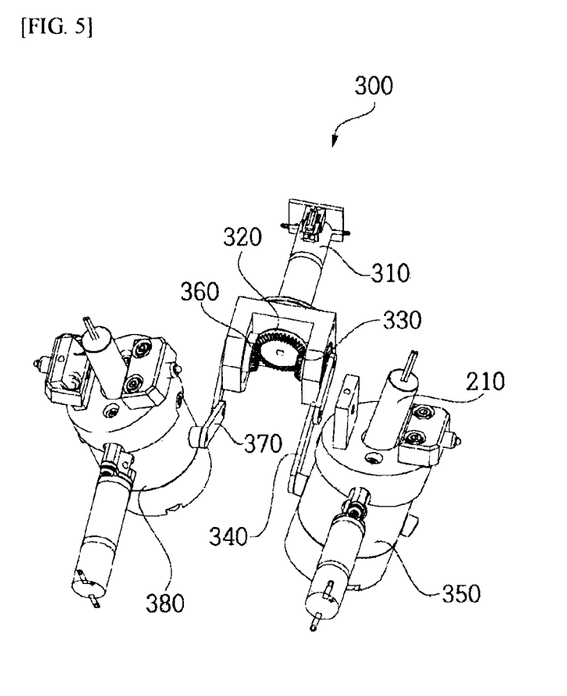
FIG. 5 is a detailed diagram illustrating the laser swing unit in the apparatus for treating athlete's foot according to the exemplary embodiment of the present invention.
Figure 6:
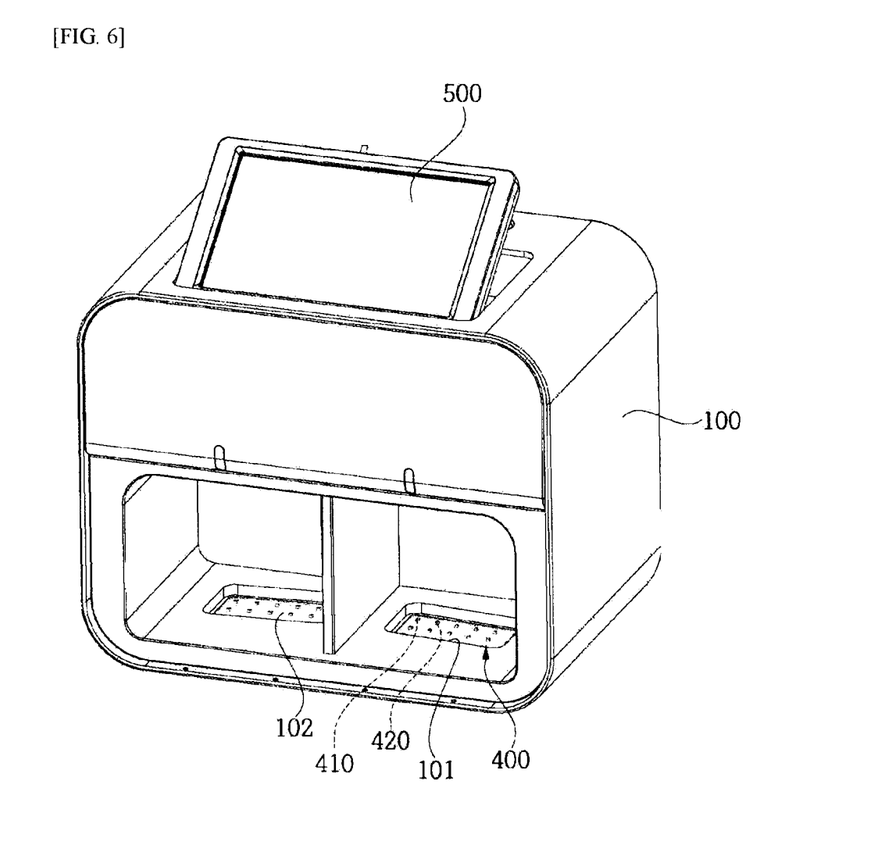
FIG. 6 is a configuration diagram illustrating an LED light source unit in the apparatus for treating athlete's foot according to the exemplary embodiment of the present invention.
Figure 7:
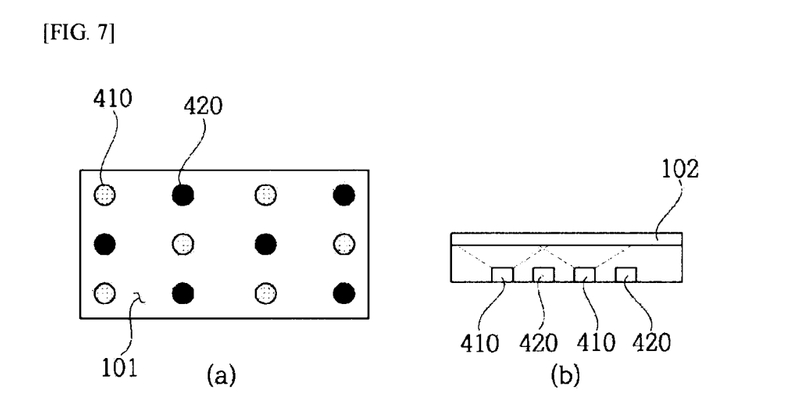
FIG. 7 is a diagram illustrating in the LED light source unit in the apparatus for treating athlete's foot according to the exemplary embodiment of the present invention, and (a) is a schematic top plan view illustrating an LED arrangement structure, and (b) is a schematic cross-sectional diagram illustrating the LED light source unit.
Figure 8:
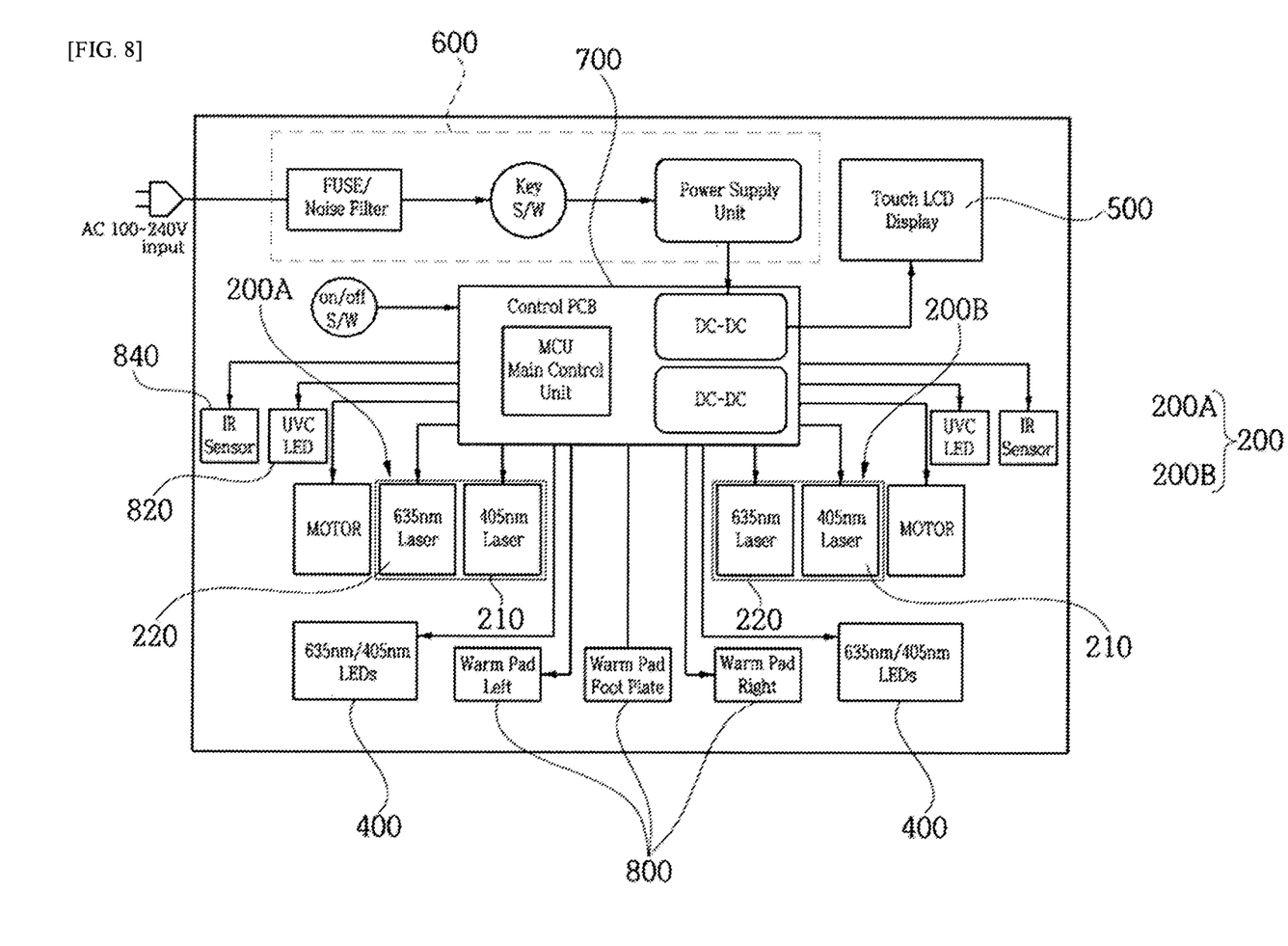
FIG. 8 is a schematic diagram illustrating the apparatus for treating athlete's foot according to the exemplary embodiment of the present invention.

In particular, as illustrated in FIGS. 4 and 5, the laser swing unit 300 may include a driving motor 310 located at an upper side of the body accommodating space part 110 and fixedly installed on the main body 100, a main bevel gear 320 coupled to a rotation shaft of the driving motor 310, a first driven bevel gear 330 cross-coupled to one side of the main bevel gear 320, a first connection link 340 of which one end is link-coupled to the first driven bevel gear 330, a first swing driving body 350 provided to swing while being link-coupled to the other end of the first connection link 340 and equipped with a first laser diode 210, a second driven bevel gear 360 cross-coupled to the other side of the main bevel gear 320, a second connection link 370 of which one end is link-coupled to the second driven bevel gear 360, and a second swing driving body 380 provided to swing while being link-coupled to the other end of the second connection link 370 and equipped with a second laser diode 220.

The laser swing unit 300 may be disposed to swing in the front and rear directions or swing in the left and right directions with respect to the laser output unit 200 depending on the direction in which the laser swing unit 300 is installed.

Herein, the laser output unit 200 and the laser swing unit 300 may be installed in a pair structure according to the number of body accommodating space parts 110 formed in the main body 100.

To describe in detail, when the first body accommodating space part 111 and the second body accommodating space part 112 are provided by disposing the body accommodating space part 110 at the left and right sides of the main body 100 and dividing the body accommodating space part 110 by the partition wall, a first laser output unit 200A and a first laser swing unit 300A may be matched and disposed at the upper side of the first body accommodating space part 111, and a second laser output unit 200B and a second laser swing unit 300B may be matched and disposed at the upper side of the second body accommodating space part 112.

In the foregoing configuration, the first laser output unit 200A and the first laser swing unit 300A, and the second laser output unit 200B and the second laser swing unit 300B may be separately controlled through a switching selection by a user or may be sometimes synchronously controlled for a simultaneous operation.

Herein, the laser swing unit 300 may be processed by a program so as to perform a swing operation for the laser output unit 200 through a basic control in the control unit 70, and the laser swing unit 300 may be used in various forms, such as the case where the laser swing unit 300 is position-fixed and used by a manipulation of a user as needed.

Herein, the laser swing unit 300 may control the number of times of rotation of the driving motor 310 or adjust a swing processing speed in the form of adjusting gear engagement ratios between the main bevel gear 320 and the first driven bevel gear 300 and between the main bevel gear 320 and the second driven bevel bear 360.

The LED light source unit 400 is mounted onto the main body 100, and is provided to emit LED light from the lower side to the upper side of the body accommodating space part 110.

The LED light source unit 400 is formed of a first LED 410 emitting LED light of a wavelength of 405 nm, and a second LED 420 emitting LED light of a wavelength of 635 nm.

In this case, the first LED 410 and the second LED 420 are provided in plural at the lower side of the bottom surface of the body accommodating space part 110, and may be disposed at an interval or be sequentially arranged alternately.

In detail, a grooved mounting part 101 recessed in the down direction is formed on the bottom surface of the body accommodating space part 110, so that the LED light source unit 400 is mounted inside the grooved mounting part 101, and the grooved mounting part 101 is covered by a tempered glass plate 102 so that the LED light is transmitted and emitted, and the tempered glass plate 102 is disposed so as to maintain the same horizontal surface as the bottom surface of the body accommodating space part 110.

To explain more, the first body accommodating space part 111 and the second body accommodating space part 112 are provided by disposing the body accommodating space part 110 at the left and right sides of the main body 100 and dividing the body accommodating space part 110 by the partition wall, the LED light source unit 400 is disposed in each of the first body accommodating space part 111 and the second body accommodating space part 112.

In this case, the first LED 410 emitting the LED light of the 405 nm wavelength and the second LED 420 emitting the LED light of the 635 nm wavelength may be controlled to alternately output the LED light according to a setting time.

Further, the first LEDs 410 emitting the LED light of the 405 nm wavelength may be disposed at an interval so that emitted light overlaps, and the second LEDs 420 emitting the LED light of the 635 nm wavelength may also be disposed at an interval so that emitted light overlaps.

Herein, as described in detail, the 405 nm wavelength and the 635 nm wavelength have the same mechanism of fungal death by photochemical reaction through the laser output unit 200, so that it is possible to further improve efficiency of the treatment of athlete's foot when the LED light source unit 400 is applied together with the laser output unit 200.

The display unit 500 is mounted on an upper surface of the main body 100, and it is preferable that the display unit 500 is configured with a touch screen so as to allow an input of a user and the like, and is the constituent element for visually displaying data processed by the control unit 700 on a screen.

The display unit 500 may be disposed in a structure accommodated in the upper surface of the main body 100, and may have a configuration that is exposed to the upper side of the main body according to the lock release when the display unit 500 is pressed by grafting an elastic locking structure, and sometimes, the display unit 500 may also be configured to be automatically set by a button manipulation by using a driving means, such as a motor.

Further, the present invention includes the configuration equipped with a camera unit 800, such as a photographing sensor, photographing the body accommodating space part 110.

Figure 9:
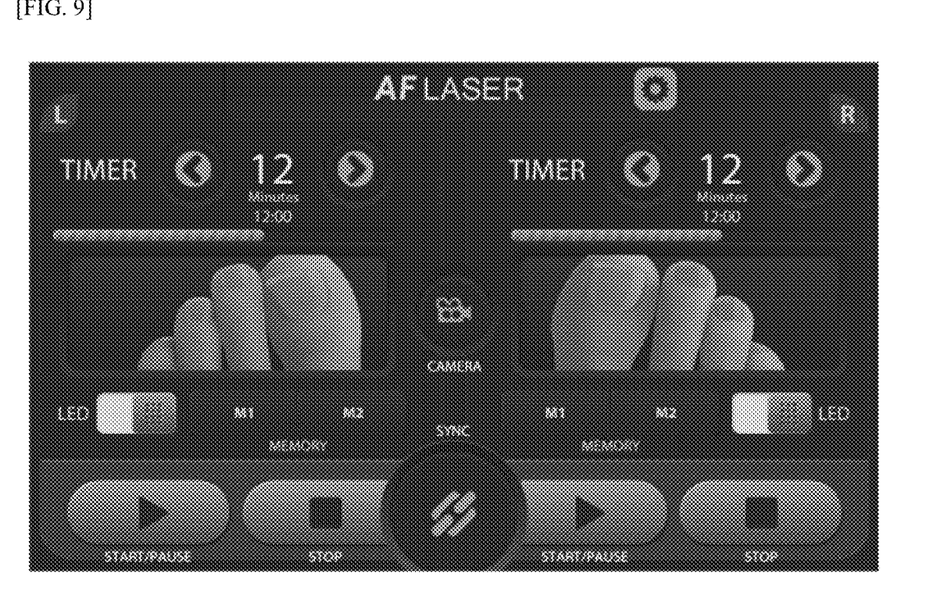
FIG. 9 is a diagram illustrating an example of a state in which photographing data of a camera unit is displayed on a screen of a display unit in the apparatus for treating athlete's foot according to the exemplary embodiment of the present invention.

In this case, the photographing data of the camera unit 800 is displayed on the display unit 500 to allow the user to monitor the treatment scene of the hand or foot in real time. Therefore, it is possible to easily adjust a treatment position of the body portion of the hand or foot.

Further, the present invention includes an opening/closing door 120 which is coupled to the main body 100 while being supported on the main body 100 to open/close the body accommodating space part 110.

In this case, the opening/closing door 120 functions as an opening/closing member that allows the body accommodating space part 110 to be opened and closed, and functions as a support for stably supporting the rear part of the foot exposed to the outside when being stepped by accommodating the foot for treating athlete's foot of the foot or toenails in the body accommodating space part 110.

The opening/closing door 120 may be provided to perform the opening/closing operation on the body accommodating space part 110 on the main body 10 through attachment/detachment using a magnet 103, and a handle may be provided on an external surface thereof.

The inner surface of the opening/closing door 120 and the bottom surface of the body accommodating space part 110 may be formed of stainless steel, titanium, or aluminum having harmless to human body, rigidity, and corrosion resistance.

That is, a stainless steel plate, a titanium plate, or an aluminum plate may be attached to the inner surface of the opening/closing door 120.

In the present invention, a warm pad 800, such as a planar heating body, may be disposed on at least one of the inner surface of the opening/closing door 120, the bottom surface of the body accommodating space part 110, and the like so as to provide heat to the user.

In the present invention, an ultraviolet (UV) LED 820 may be mounted onto the main body 100 so as to self-sterilize the inside of the body accommodating space part 110.

In this case, it is preferable that the UV LED 820 is the UV-C-type LED, and may be used while being installed on the lateral wall, the inner wall, and the like forming the body accommodating space part 110, and enables the contamination prevention and clean use of the apparatus.

In the present invention, an IR sensor 840 may be mounted onto the main body 100 so as to detect the entrance or location of the hand or foot in the body accommodating space part 110 when the hand or foot enters or is located in the body accommodating space part 110.

In this case, the IR sensor 840 may be located at the upper end portion or the side portion of the starting part of the body accommodating space part 110, when the field of vision in the body accommodating space part 110 is not secured, the IR sensor 840 has the form of driving and controlling the LED light source unit 400, thereby checking and securing the treatment position for the treatment.

Therefore, through the apparatus 1 for treating athlete's foot according to the present invention including the foregoing configuration, the body portions of the hand and foot having athlete's foot are irradiated with a light source output of a laser and/or an LED having a wavelength band useful for treatment of athlete's foot, thereby very effectively treating athlete's foot generated on the hand or foot, nails, or toenails, and enabling users to conveniently use the apparatus.

The exemplary embodiment described above are merely illustrative of exemplary embodiments of the present invention, and are not limited to these embodiments, and various modifications and variations may be made by those skilled in the art within the technical spirit and claims of the present invention. It will be said that the modifications and variations belong to the scope of the technical rights of the present invention.

What is claimed is:

1. An apparatus for treating athlete's foot, the apparatus comprising:
    a main body having at least one body accommodating space part to accommodate a body portion of at least one of a hand and foot;
    a laser output unit mounted onto the main body, and provided to emit laser light from an upper side to a lower side of the body accommodating space part; and a laser swing unit positioned at the upper side of the body accommodating space part and fixedly installed on the main body, wherein the laser swing unit drives the laser output unit to swing on the main body, wherein the laser output unit includes a first laser diode emitting laser light of a 405 nm wavelength and a second laser diode emitting laser light of a 635 nm wavelength.

2. The apparatus of claim 1, further comprising:

an LED light source unit mounted onto the main body and configured to emit LED light from the lower side to the upper side of the body accommodating space part, wherein the LED light source unit includes a first LED emitting LED light of a 405 nm wavelength and a second LED emitting LED light of a 635 nm wavelength, and the first LED and the second LED are provided in plural to be disposed at intervals and sequentially arranged alternately.

3. The apparatus of claim 1, wherein the laser swing unit includes:

a driving motor fixedly installed on the main body;

a main bevel gear coupled to a rotation shaft of the driving motor;

a first driven bevel gear cross-coupled to one side of the main bevel gear;

a first connection link of which one end is link-coupled to the first driven bevel gear;

a first swing driving body link-coupled to the other end of the first connection link to perform a swing operation and mounted with the first laser diode;

a second driven bevel gear cross-coupled to the other side of the main bevel gear;

a second connection link of which one end is link-coupled to the second driven bevel gear; and a second swing driving body link-coupled to the other end of the second connection link to perform a swing operation and mounted with the second laser diode.

4. The apparatus of claim 2, wherein the LED light source unit is provided within a grooved mounting part recessed in a down direction on a bottom surface of the body accommodating space part, and the grooved mounting part is covered by a tempered glass plate so as to allow LED light to transmit and emit, and the tempered glass plate is disposed so as to maintain the same horizontal surface as the bottom surface of the body accommodating space part.

5. The apparatus of claim 1, wherein a display unit is mounted on an upper surface of the main body, a camera unit photographing the body accommodating space part is mounted, and the display unit is installed to display photographing data of the camera unit to allow a user to monitor a treatment scene of the hand or foot in real time and allow the user to adjust a treatment position of the hand or foot.

6. The apparatus of claim 1, wherein an ultraviolet (UV) LED is mounted onto the main body to self-sterilize an inside of the body accommodating space part.

7. The apparatus of claim 1, wherein an opening/closing door is provided on the main body, and functions as an opening/closing member to open and close the body accommodating space part, and functions as a support for stably supporting a rear part of the foot exposed to the outside when being stepped by accommodating the foot for treating athlete's foot of the foot or toenails in the body accommodating space part.

8. The apparatus of claim 7, wherein an inner surface of the opening/closing door and a bottom surface of the body accommodating space part are made of a stainless steel or titanium material having harmless to human body, rigidity, and corrosion resistance.

9. The apparatus of claim 1, wherein the opening/closing door is provided to perform an open/close operation on the main body through attachment/detachment by a magnet.

10. The apparatus of claim 8, wherein a planar heating body is disposed in at least one of the opening/closing door and the body accommodating space part so as to provide heat.

11. The apparatus of claim 1, wherein a curtain part is provided at an entrance part of the body accommodating space part.

12. The apparatus of claim 2, wherein the first LED emitting the LED light of the 405 nm wavelength and the second LED emitting the LED light of the 635 nm wavelength alternately output the LED light according to a setting time.

13. The apparatus of claim 12, wherein the first LEDs emitting the LED light of the 405 nm wavelength are disposed at intervals so that the emitted light overlaps, and the second LEDs emitting the LED light of the 635 nm wavelength are disposed at intervals so that the emitted light overlaps.

14. The apparatus of claim 1, wherein the body accommodating space part is disposed at left and right sides in the main body and is divided by a partition wall to be provided with a first body accommodating space part and a second body accommodating space part, a first laser output unit and a first laser swing unit, and a second laser output unit and a second laser swing unit are matched and provided to an upper side of the first body accommodating space part and an upper side of the second body accommodating space part, respectively, and the first laser output unit and the first laser swing unit, and the second laser output unit and the second laser swing unit are separately controlled or synchronously controlled.

15. The apparatus of claim 1, wherein an IR sensor is mounted on the main body to detect entrance or location of the hand or foot when the hand or foot enters or is located in the body accommodating space part.

* * * * *